United States Patent [19]

de Jonge et al.

[11] 4,339,699
[45] Jul. 13, 1982

[54] MOTOR CONTROL SYSTEM FOR USE IN AN APPARATUS FOR PERFORMING TESTS AND MEASUREMENTS ON LIQUID SAMPLES

[75] Inventors: Jan H. de Jonge, Dieren; Johannes H. L. Hogen Esch, Aalten, both of Netherlands

[73] Assignee: Vitatron Scientific B.V., Dieren, Netherlands

[21] Appl. No.: 179,502

[22] Filed: Aug. 19, 1980

[51] Int. Cl.³ ............................................. G05B 13/00
[52] U.S. Cl. .................................... 318/561; 318/596; 318/603; 318/610; 318/621; 318/640
[58] Field of Search ............... 318/603, 640, 596, 610, 318/561, 621, 622, 611

[56] References Cited

U.S. PATENT DOCUMENTS

3,741,474  6/1973  Kawada et al. ..................... 318/610
3,914,677  10/1975  MacWade et al. .................. 318/640

Primary Examiner—J. V. Truhe
Assistant Examiner—Eugene S. Indyk
Attorney, Agent, or Firm—Woodcock, Washburn, Kurtz, Mackiewicz & Norris

[57] ABSTRACT

There is provided a motor control system adapted for use, for example, with a sample analyzer, having means for generating signals representative of motor movement, and a logic circuit for analyzing the motor movement signals to determine increments of movement and the direction of movement. Digital circuitry is also provided for tracking the actual motor position as it is moved in either a forward or reverse direction, and comparing the tracked position with a programmed destination position. When and only when the motor is within a predetermined range of the destination position is a variable control generated, causing braking of the motor so that it stops exactly at the programmed destination position.

4 Claims, 11 Drawing Figures

MOTOR CONTROL SYSTEM FOR USE IN AN APPARATUS FOR PERFORMING TESTS AND MEASUREMENTS ON LIQUID SAMPLES

RELATED APPLICATIONS

The present application relates to Ser. No. 893,389 filed Apr. 11, 1978, entitled "An Apparatus for Performing Tests and Measurements on Liquid Samples."

BACKGROUND OF THE INVENTION

The present invention relates in general to an apparatus for performing tests and measurements on various samples such as sera, and in particular, it relates to a novel motor control means for accurately controlling a reversible electric motor in an apparatus for performing such tests and in other, more general applications. In the related application, an apparatus is disclosed for performing tests and measurements on various liquid samples, in particular sera. The apparatus employs three identical juxtaposed trays each of which are provided with a plurality of receptacles. The first tray includes storage vessels for samples to be tested. The second and third trays serve as processing vessels. Situated above the trays are three independently movable pipettes. Each of the pipettes is situated on carriages which are translatable in a horizontal plane above the trays to position the pipettes over particular receptacles. The pipettes are also translatable in the vertical direction for adding or discharging sera sample, reagents, etc. into particular receptacles. Movement of each of the pipettes in the horizontal and vertical directions is accomplished by means of small electric motors.

It is extremely important that the electric motors utilized for translation of the pipettes be able to operate at high speed and with extreme accuracy. Moreover, it is essential that such electric motors be extremely compact.

It is an object of the present invention to provide a motor control means for accurately controlling a reversible electric motor in the aforementioned and other apparatus which is capable of high speed operation and yet which is extremely accurate.

It is another object to provide such a motor control means which is very compact.

It is another object of this invention to provide means for continuously and unambiguously tracing the position of a motor, and thus the location of the element being driven thereby, as the motor is driven in either a forward or reverse direction.

It is another object of this invention to provide a drive control for a motor, whereby the motor is normally driven at a maximum speed toward its destination and is controlled to decelerate only when it is within a predetermined range from the destination.

It is another object of this invention to provide a digital motor control adaptable to drive a motor through any desired range of steps, or increments, and to control change of motor speed within a range of increments which can be selected as a design parameter.

SUMMARY OF THE INVENTION

The foregoing objectives are achieved by a system where each moveable element is driven by a rotatable shaft coupled to a reversible electric motor. Axially aligned with the shaft are a first light source-light detector pair optically coupled to one another along a first optical path and a second light source-light detector pair optically coupled to one another along a second optical path. A means, preferably a rotating disk, is provided which is coupled to the shaft and which periodically interrupts the optical paths, generating separate square wave signals 90° out of phase with each other. The signals are inputted to a converter which logically analyzes the up-down sequences of the two signals in relation to each other, and provides an up or down pulse each signal cycle corresponding to whether the motor is going forward or reverse. An up-down counter is provided which is responsive to the up and down signals for storing a count proportional to the current angular position of the shaft. Further, a register (latch) is provided for storing a number proportional to the desired or programmed angular shaft position, and thus the programmed element position. A difference circuit responsive to the counter and register is provided which generates a signal corresponding to the difference between the current and desired positions. A drive circuit is provided which drives the motor at full speed except when the difference signal indicates that the motor is within a predetermined control range, at which time the motor movement is controlled as a function of motor position.

A separate motor, is provided for moving each pipette in the X and Y respectively, and each has such a motor drive control system.

BRIEF DESCRIPTION OF THE DRAWINGS

The present invention is more fully understood by reference to the accompanying drawings in which.

DETAILED DESCRIPTION OF THE PREFERRED EMBODIMENT

Figure 1:
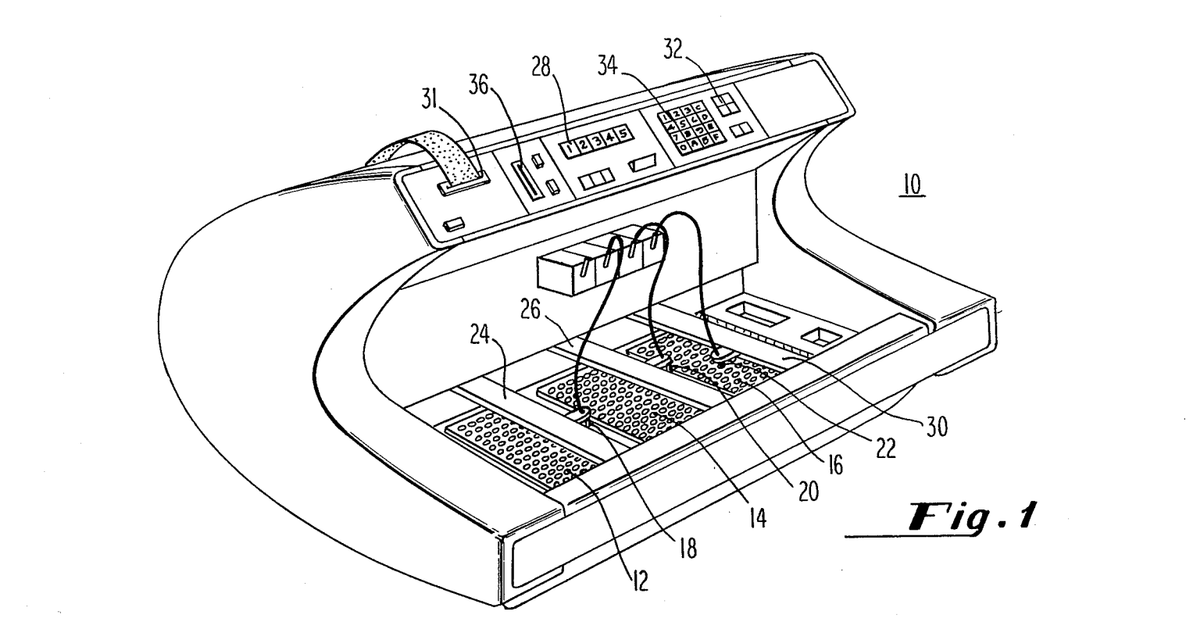
FIG. 1 shows an overall view of an apparatus for performing tests and measurements of various liquid samples, in particular sera.

Referring now to FIG. 1, a sample analysis device is shown generally at 10 for performing tests and measurements on various liquid samples, in particular sera. The device 10 employs three juxtaposed trays 12, 14 and 16 each containing a large plurality of receptacles. The receptacles positioned in the first tray 12 are storage vessels for samples to be tested. The receptacles situated in the second and third trays serve as processing stations in which reagents are added to the sample after having been transferred there. Transfer between and among various receptacles is accomplished by means of pipettes 18, 20 and 22. Movement of the pipettes 18, 20 and 22 is by means of carriages 24, 26 and 30 respectively. Each of the carriages 24, 26 and 30, is controlled by means of an electric motor of the type shown in FIG. 2 and which will be more fully described below. Movement of the pipettes in the vertical direction is also controlled by motors of this type.

The device 10 is provided with a photometer, not shown, for performing various measurements. The results may be indicated upon a digital display 28 or a cathode ray tube, and/or a printer 31. Furthermore, device 10 is provided with an operating keyboard 32, an entering keyboard 34, and a reading and writing device 36 for magnetic cards or tapes.

Figure 2:
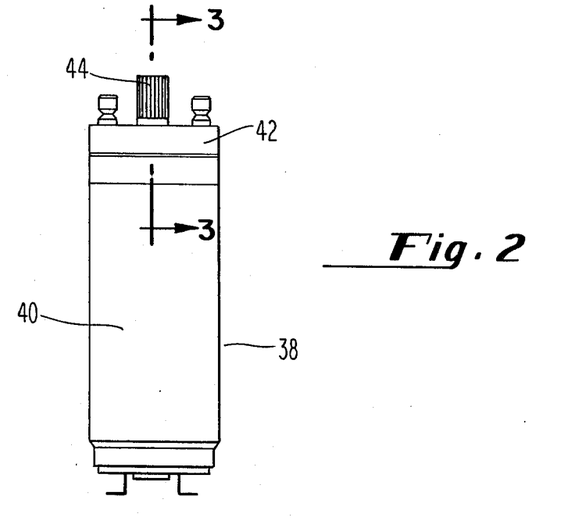
FIG. 2 is an elevational view in full size of an electric motor utilized for controlling the movements of pipettes shown in FIG. 1.

Because the movement of the various pipettes 18, 20 and 22 among the various receptacles must be very accurately controlled, it is essential that the motor control unit for the drive motors therefore be extraordinarily accurate. Such a drive motor is shown in FIG. 2 generally at 38. The motor 38 includes a housing 40 situated upon a base 42. Projecting from the base and coupled to the motor situated within the housing 40 is a shaft 44 to which are attached cables for driving the aforementioned carriages and pipettes.

In the preferred embodiment of the sample analysis device of this invention, 14 motors with associated controls are utilized. Three motors are used for moving the three carriages in the x direction; three motors are used for moving the pipettes in the y direction; six motors are used to drive the pistons of pumps which fill and empty the pipettes; and two motors are used for changing the wavelength settings for the dual lights used in the photometer. In the description that follows, it will be assumed that the motor is driving one of the carriages in the x direction, i.e. normal to the length of the carriage as illustrated in FIG. 1. In an illustrative embodiment the carriage 18 may be driven linearly 128 steps from left to right, with a step being defined as the lineal distance between adjacent tray receptacles, or positions. Also, the carriage 18 has a vane, not shown, adapted to intercept a switch at a fixed reference position, so as to provide a position signal for informing when the carriage and thus the motor is at a predetermined location. This is a standard means of providing a position reference signal to the motor control circuitry, for reasons discussed in connection with FIG. 6.

Figure 3:
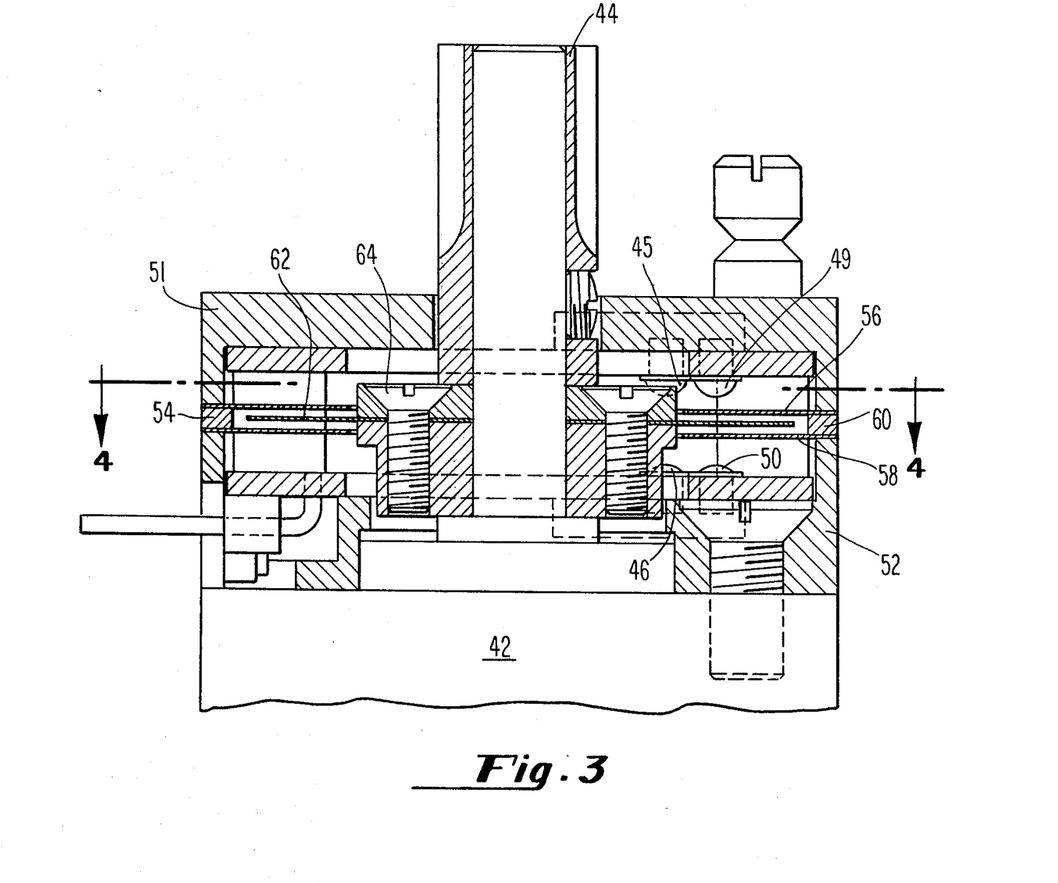
FIG. 3 is a cross-sectional view taken along line 3—3 of FIG. 2.

Referring now to FIG. 3, the base 42 of the motor 38 will be more fully described. In accordance with an important aspect of the present invention, the base 42 includes a first light source-light detector pair including a light emitting diode 45 and a phototransistor 46 which are optically coupled to one another along a first optical path. The base 42 also includes a second light source-light detector pair including a light emitting diode 49 and a phototransistor 50. The second light source-light detector pair are coupled to one another along a second optical path. The light emitting diodes 45 and 49 are situated in and affixed to a first housing portion 51 of the base 42 while the phototransistors 46 and 50 are situated in and affixed to a second housing portion 52. The first and second housing portions 50 and 52 are affixed to one another such that a mask assembly shown generally at 54 is situated therebetween. The mask assembly 54 includes a first mask means 56 in a plane perpendicular to the axis of the shaft 44 and a second mask means 58 in a plane parallel to the first mask means 56. Mask means 56 and 58 are separated from one another by means of a spacer 60. Details of the mask assembly 54 will be provided below; however, suffice it to say that situated between the first and second mask means 56 and 58 is a means for periodically interrupting one, then neither then the other and finally both of the optical paths. This interruption means preferably comprises a disk 62 which is mounted to the shaft 44 by means of screws 64 so as to be rotable with the shaft 44. The disk 62 contains a plurality of slits therein which alternately permit light to travel along the first and then the second optical path. The aforementioned mask means 56 and 58 each comprise a pair of narrow slits 57 and 59 respectively, situated in the first and second optical paths so as to preclude stray light from entering these paths.

Figure 4:
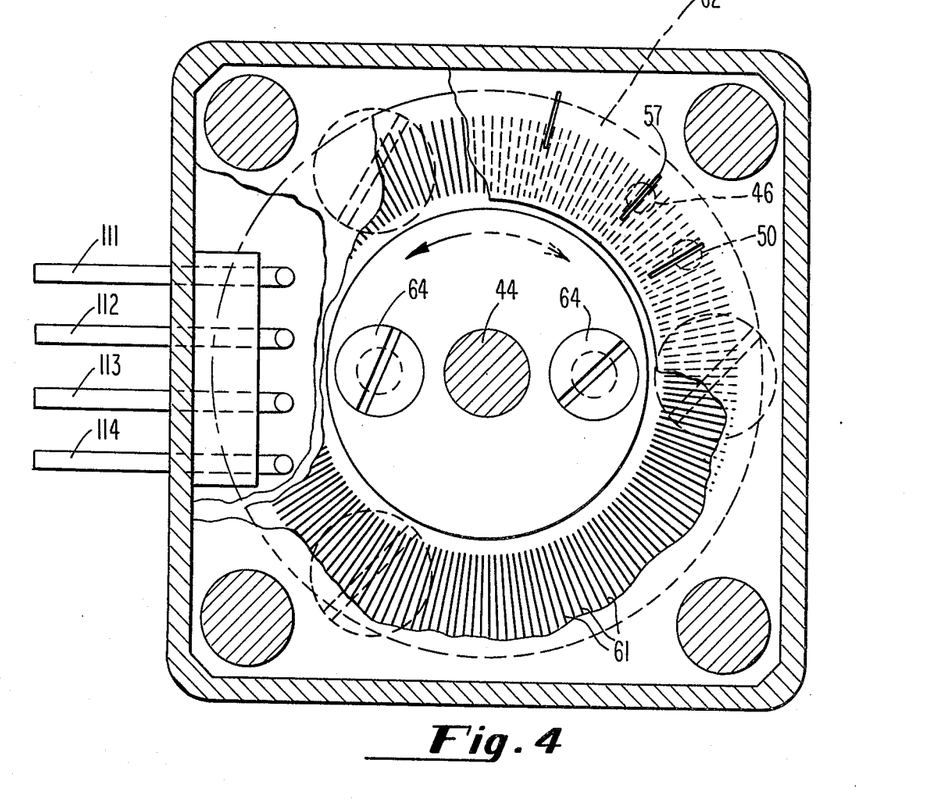
FIG. 4 is a cross-sectional view taken along line 4—4 of FIG. 3.

Referring now to FIG. 4, details of the rotating disk 62 are illustrated. As seen in FIG. 4, the rotating disk 62, which is coupled to the shaft 44, preferably includes a large plurality of slits 61. The slits are radially disposed in an arcuate pattern about the circumference of the disk 62, the arcuate pattern being concentric with the disk. In the preferred embodiment, 100 slits 61 are formed in the disk 62, the slits being disposed at an angle of 3.6 degrees with respect to one another. The slits have a width that is equal to the width between them, such that light detectors 46 and 50 produce signals of 50% duty cycle when the disk 62 is rotating. In the preferred embodiment, the first and second optical paths are axially parallel to and radially disposed from the center of the shaft 44, and angularly displaced from each other. Also, as shown in FIG. 4, electrical leads 111, 112, 113 and 114 are provided for directing current to light sources 45 and 49 and for transmitting the output from light detectors 46 and 50 to a circuit to be described below.

Figure 5:
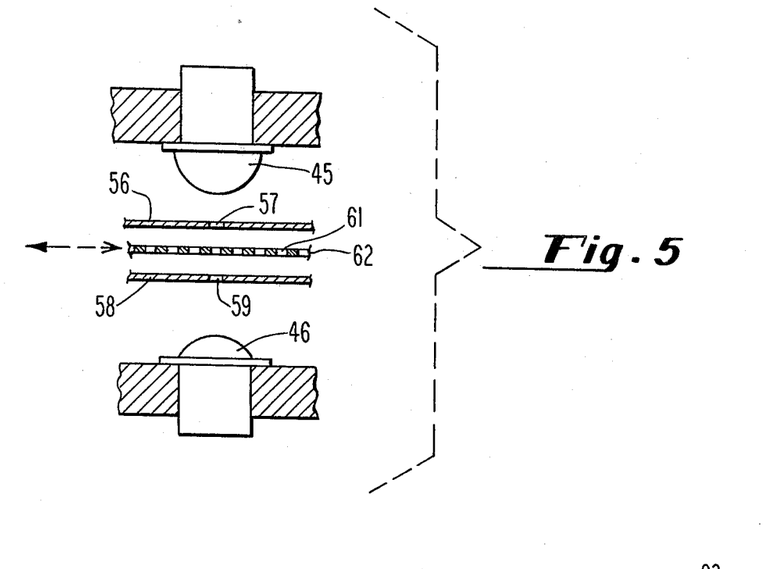
FIG. 5 is a detailed schematic view of one of the optical paths shown in FIG. 3.

Referring now to FIG. 5, the first optical path including light source-light detector pair 45 and 46 is illustrated. That optical path includes the light emitting diode 45 separated from the phototransistor 46 by means of mask means 56 and 58. The mask means 56 and 58 have slits therein 57 and 59 respectively. Situated intermediate the mask means 56 and 58 is the rotating disk 62 having slits 61 therein as shown. It is seen that rotation of disc 62 in either direction causes periodic light pulses at detector 46, causing generation of a first square wave signal (50% duty cycle). A corresponding arrangement with pair 49, 50 generates a second square wave which is 90° out of phase with the first signal.

Figure 6:
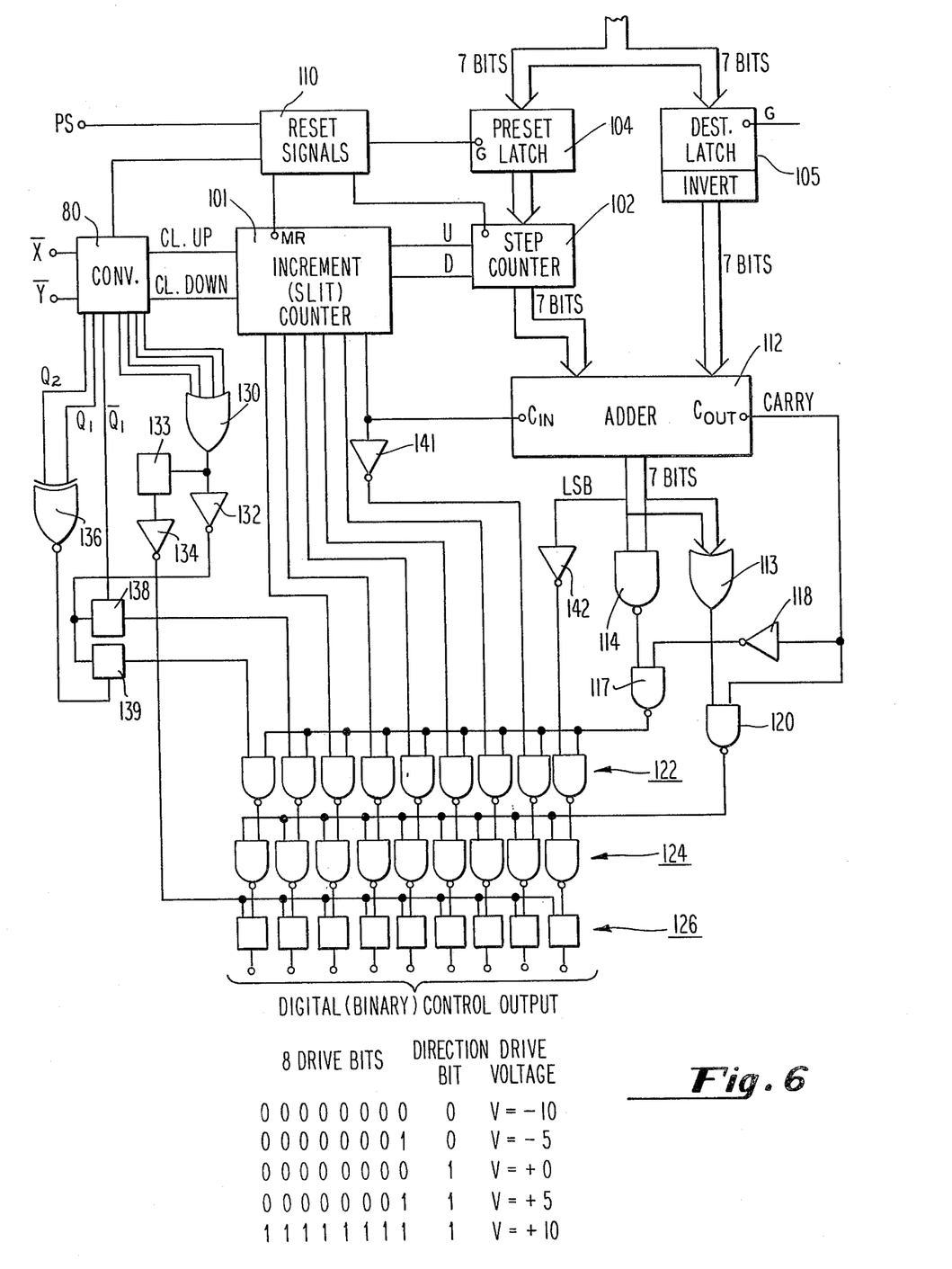
FIG. 6 is a schematic circuit diagram of the digital portion of the motor control for driving a motor in the sample analysis device of this invention.

Referring now to FIG. 6, there is seen a block diagram showing the overall logic circuitry for providing a digital control output as a function of the two detector signals x and y which are produced by the two photodetectors mounted on the base of the motor. As an overview, the circuitry of FIG. 6 takes the x and y signals, inverted to $\bar{x}$ and $\bar{y}$, and converts them in converter circuit 80 to provide clock up and clock down signals every time the motor has rotated through a slit cycle, e.g., 3.6° for a disc having 100 equally spaced slits. The signals from converter 80 increment the count in counter 101, which keeps track of the number of slits that the motor has rotated in the course of a step, i.e., in going from a first position toward a next position. Counter 101 is a six bit binary coder, corresponding to the arrangement of 64 slits on the motor disc being equal to one step, i.e. when the motor rotates 64 slits the carriage has moved from one position to a next position.

Each time the motor has moved one step, a signal is produced which steps counter 102 up by one count or down by one count, depending upon whether the motor is going in the forward or reverse direction. Step counter 102, which may be initially preset to a programmed value supplied by a microprocessor through preset latch 104, keeps track of the current step location of the motor, i.e., the current location of the carriage which is being driven toward a given destination. The destination, supplied also from a microprocessor, is inputted as a seven bit signal to destination latch 105. The seven bit binary signal from step counter 102 is connected to adder 112, and the inverted seven bit binary count from latch 105 is gated as a negative input to adder 112, which therefore provides a difference between the present location (as indicated in step counter 102) and the destination location (as indicated by the seven bit output of latch 105). As the motor moves the carriage from step to step, the differential between the present location and the programmed destination is computed in adder 112 by adding the complement of the destination signal to the current location signal. It is to be noted that the reset signals are suitably provided by circuitry designated at block 110, to set the slit counter 101, and to latch a referencing count, or preset count into step counter 102 at the time that the carriage has been moved to a preset location. As indicated previously in the specification, a vane-switch combination may be used to provide a preset signal which gates the preset information (provided by the microprocessor) through latch 104 to counter 102 when the motor has moved the carriage to the preset location. As discussed below, until the actual motor position, or carriage location is within one step of the destination position, the digital output is such as to drive the motor in either a forward or reverse direction at full speed. A large portion of the remaining logic circuitry of FIG. 6 carries out the function of determining when the actual position is within one step of the destination position, at which time a variable digital (binary) control output is produced through latch 126. The control circuitry defines a control range which is one step in the plus or minus direction from the destination location, and only when the motor has moved to within such control range is there a variable digital output. The manner in which this is achieved is discussed below after the examination of the operation of converter 80.

Figure 7:
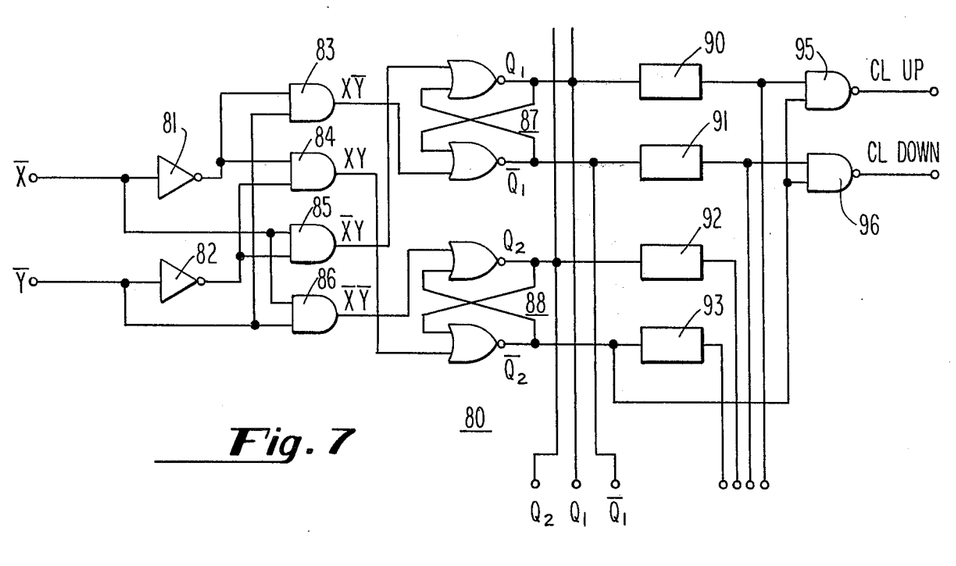
FIG. 7 is a circuit diagram of the converter in FIG. 6.
Figure 8:
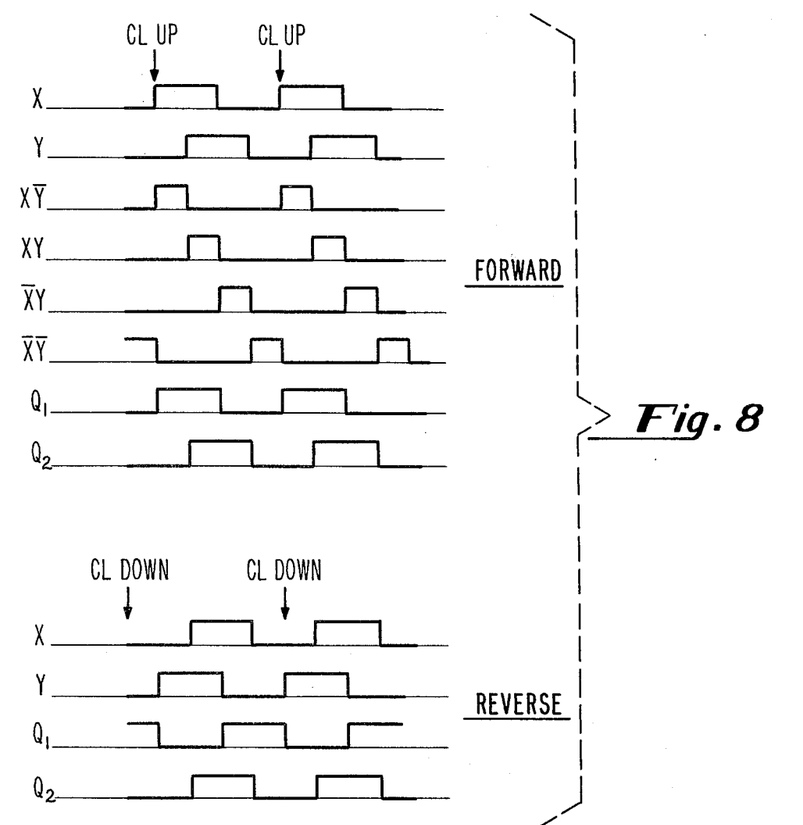
FIG. 8 shows signal waveforms at selected points in the circuit of FIG. 7.

Referring now to FIG. 7 there is shown a schematic diagram of the converter 80 used to provide the clock up and clock down signals. This converter has a memory, or hysteresis effect, such that it can determine from the $\bar{x}$ and $\bar{y}$ wave forms whether the motor is going in a forward direction, thereby producing a clock up signal, or a reverse direction, thereby producing a clock down signal. Analysis of the circuit diagram of FIG. 7 together with the timing wave forms of FIG. 8 illustrates the manner of operation.

The $\bar{x}$ and $\bar{y}$ signals, which are developed at the two photodetectors, are inputted to inverters 81 and 82 respectively. The output of inverter 81 and the $\bar{y}$ signal are inputted to AND gate 83, providing the x $\bar{y}$ signal which is connected to the set input of flip flop 87. The output of inverter 81 and the output of inverter 82 are inputted to AND gate 84, the output being the XY signal which is connected to the set input of flip flop 88. The $\bar{x}$ signal and the output of inverter 82 are connected to AND gate 85, providing the $\bar{x}$ y signal which is connected to the reset terminal of flip flop 87. The $\bar{x}$ signal and the $\bar{y}$ signal are connected as inputs to AND gate 86, providing the $\bar{x}$ $\bar{y}$ signal which is inputted to the reset terminal of flip flop 88. As is seen from the connections from flip flops 87 and 88 to monostable circuits 90-93, circuit 90 provides an output pulse when $Q_1$ goes high; circuit 91 provides an output pulse when $Q_1$ goes low; circuit 92 provides an output pulse when $Q_2$ goes high; and circuit 93 provides an output pulse when $Q_2$ goes low.

The output of circuit 90 is connected to a first input of NAND gate 95, the other input to gate 95 being taken from $\overline{Q_2}$. There is a negative going output pulse produced from circuit 95, which is the clock up pulse, when $Q_1$ is set at the same time that $Q_2$ is reset. From the timing diagrams of FIG. 8, it is seen that this occurs when the disc is being moved in the forward direction, but it does not occur when the disc is being moved in the reverse direction. The output of circuit 91 is connected to a first input of NAND gate 96, while the second input is connected to the $\overline{Q_2}$ terminal of flip flop 88. A negative going pulse is produced at the output of gate 96, being the clock down pulse, when and only when $Q_1$ is reset while $Q_2$ is low. As seen from the timing diagrams of FIG. 8, this occurs only when disc is rotating in a reverse direction, and does not happen when the disc is rotating in a forward direction.

It is thus seen that the circuitry of this converter provides a logical analysis of the timing with which the $\bar{x}$ and $\bar{y}$ signals occur; since this timing is different depending upon whether the disc is going in a forward direction or a backward direction, a different result is obtained depending upon the direction. It is to be noted that this logical analysis, includes a hysteresis characteristic of the converter, which makes the operation independent of the sharpness of the leading and trailing edges of the $\bar{x}$ and $\bar{y}$ signals. Even though there may be ringing at the edges of the signals, the logical analysis provided by the circuit prevents any production of a clock up or clock down pulse except when the correct timing cycle has been detected, thus making certain that the disc is counted accurately each cycle and making certain that there is no ambiguity in detecting the forward and reverse directions.

Returning now to FIG. 6, the remaining circuitry which provides the digital control output as a function of the x and y photodetector inputs, for precise control of the motor to the destination location, is seen. This analysis is most clearly understood by considering FIG. 6 in combination with FIGS. 9A and 9B as well.

Figure 9A:
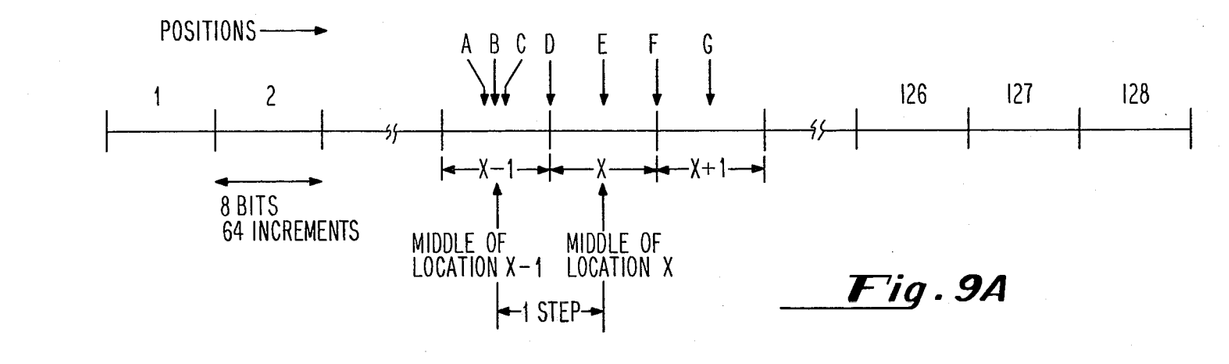
FIG. 9A is a diagram which illustrates the control range used in the motor control of FIG. 6.

As diagrammed in FIG. 9A, the motor control of this invention is designed to move the carriage to the middle of the destination position. In FIG. 9A, this position is indicated as a position X, and the middle of location X is indicated by the arrow from the letter E.

The position just before X is designated as X-1. As indicated, the motor in the illustration of the preferred embodiment has a range of 128 steps through which it can be moved. Each step corresponds to 64 slit positions, which in the digital circuitry can be represented as a 6 bit signal. The control circuitry of FIG. 6 is designed so that, for the example where the motor is at a position below the destination position, the motor is moved at full drive speed until the middle of position X-1 is reached. During the step from the middle of position X-1 to the rest point at the middle of position X, the motor control signal is changed so as to bring the motor to rest precisely when it reaches the middle of position X. If the carriage has been proceeding forward, e.g., from location 0 to location 33, when the carriage reaches the middle of location 32 (at which time increment counter 101 is half filled—the first five least significant bits are 0 and the most significant bis is 1), the control signal outputted from latches 126 begins to vary so as to control the motor to stop when the carriage is located in the middle of location 33.

Referring back to FIG. 6, the four quadrants which make up one detector cycle, corresponding to rotation of the motor by one slit, are designated as the two least significant bits ($0_0$ and $0_1$) at the binary control. These bits are determined by converter outputs Q1, Q2 and $\overline{Q1}$. As seen, Q1 and Q2 are coupled to exclusive—or circuit 136, the output of which is inputted to the D terminal of D type flip flop 139. The $\overline{Q1}$ signal is inputted to the D terminal of D type flip flop 138. Both flip flops are clocked by any one of the 4 quadrant signals outputted from the converter and passed through OR gate 130 and inverter 132. The outputs of flip flops 138 and 139 are connected to the two least significant NAND gates of gate array 122. Each output from one of the monostable circuits 90-93 of converter 80, which is passed through OR gate 130, is also inputted to a monostable circuit 133, the output of which is connected through inverter 134 to gate the latches 126. This arrangement provides for proper timing, and insures that there is a change in the digital control output only after each binary signal has passed through the entire circuit and the circuit is stabilized.

Adder circuit 112, which provides the difference between the actual position as recorded in counter 102 and the destination position as provided from latch 105, provides a seven bit binary output which is inputted to both NAND gate 114 and OR gate 113. Adder 112 receives a carry in signal, $C_{in}$, from the most significant bit of increment counter 101. This means that when increment counter 101 reaches the mid point of its count of a step, the $C_{in}$ signal is inputted to adder 112. This causes the adder to increase by 1 its actual count, the same as though step counter 102 had been incremented by 1. Likewise, a carry out signal, $C_{out}$, is generated by adder 112, which is a logic 1 when the destination is lower than the current position, and a logic 0 when the destination is higher than the current position. The carry out signal is coupled to the input of inverter 118, and also to one of the inputs of NAND gate 120. The output of OR gate 113 is connected to the other input of NAND gate 120, the output of which is connected as a control signal to the array 124 of NAND gates. The output of NAND gate 114 is connected as a second input to NAND gate 117, the output of which is connected as a control signal to each of the NAND gates of array 122. It is to be observed that NAND gate 114 acts as a "0" detector. When the destination is higher than the current position, and one or more 0's is detected through NAND gate 114, the output of NAND gate 117 is low. Under the circumstances none of the 8 input signals connected to array 122 can be gated through. However, when the carriage comes within a step of the destination, adder 112 produces all ones at its output, and the output of NAND gate 117 goes high. Thus, for the destination higher than the position, as long as the motor is driving toward the position but is not within a step of the target position, the output of NAND gate 117 is low and this disables array 122, holding the output from latches 126 such that a maximum driving signal is provided to the motor. As soon as the motor comes within one step of the target location, the output from NAND gate 117 switches, enabling the signals from increment counter 101, as well as the two least significant bits from converter 80, to be passed through and latched through array 126 to the digital output. Conversely, when the destination is lower than the current position, but more than a step away, the output from NAND gate 120 is low, disabling array 124 and producing at the output of latch array 126 a signal which drives the motor in the opposite direction at a maximum speed. When and as the motor comes within one position of the target, the output from gate 120 switches, and the position signals from the converter and the increment counter are gated through. Since the control range starts at the middle of a step, the most significant bit from counter 101 is inverted through 141 before being connected through to provide the most significant control bit in the control output. The least significant bit output from adder 112 is inverted through circuit 142 and inputted into the ninth NAND gate of array 122, to provide the $0_8$ bit, which controls whether the motor is driven in a reverse or forward direction. As seen in the table directly below latches 126, the drive direction bit changes depending upon whether the motor is below or above the target location.

Figure 9B:
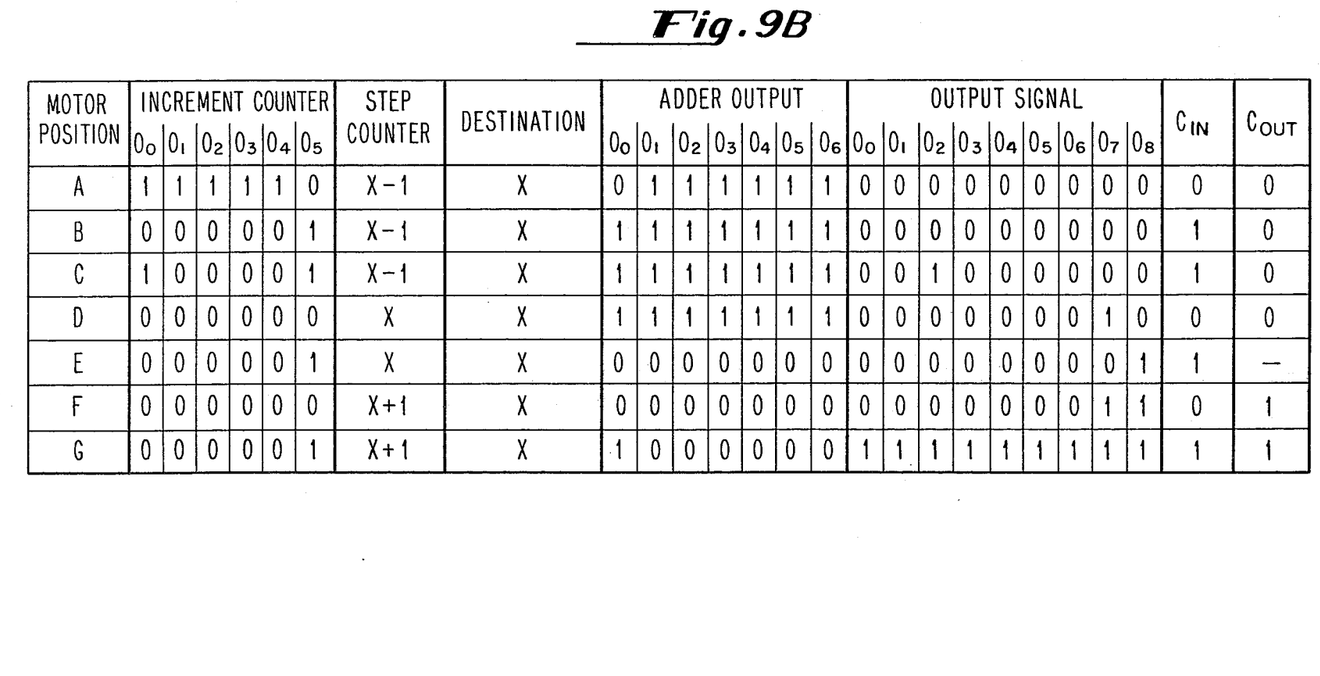
FIG. 9B is a table which illustrates data counts and signals at different places in the motor control circuit of FIG. 6.

Referring now to FIG. 9B, and with reference also to FIG. 9A, the following statements are made concerning the illustrated motor positions:

a. Motor in position X—1, but one slit before middle of X—1. Motor on full forward drive.
b. Motor at middle position X—1. Start of control range when motor proceeding forward to destination.
c. Motor advanced to one slit forward of middle of location X—1. Output signal starts to change toward 0, causing deceleration.
d. Motor at lower edge of destination position X. Most significant bit ($0_7$) of the eight control bits has changed from 0 to 1, so control output has changed halfway to 0 level.
e. Motor at middle of destination location; control voltage has gone to 0 (but direction—$0_8$—has changed), so motor stops; note that if the motor carries past the destination, a control voltage is developed which moves it back.
f. Motor at forward edge of destination position (X) and lower edge of next position (X+1).
g. Motor at middle of step just forward of destination (X+1).

Figure 10:
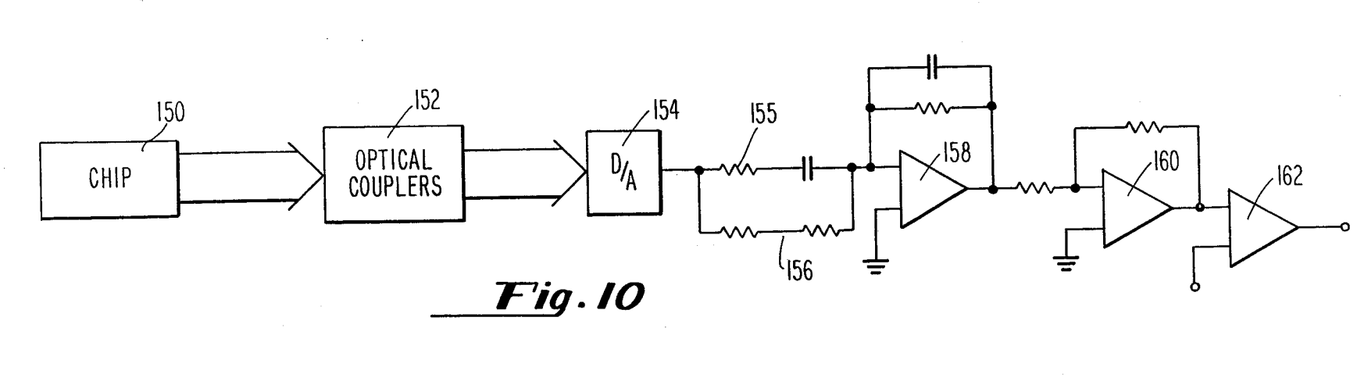
FIG. 10 is a circuit diagram showing the circuitry for generating the analog motor drive signal from the digital output of the circuit of FIG. 6.

Referring now to FIG. 10, chip 150 contains the control circuitry of FIG. 6, and provides the digital output signal, which is a nine bit signal, to optical couplers 152. The output of couplers 152 is inputted to digital to analogue circuit 154, which translates the digital signal to an analogue signal. Note that as long as the motor is more than one step away from the destination location, the analogue signal is a constant plus or minus voltage, depending upon the direction in which the motor is being driven. The analogue signal from circuit 154 is coupled to the input circuits 155, 156 of operational amplifier 158. Input circuit 155 provides a differentiation signal which causes braking when the motor is in the control range, while input circuit 156 provides the linear or static signal. As the binary signal changes linearly in response to movement of the motor through the one step control range increment by increment, the differential signal generated by circuit 155 is opposite in polarity to the linear signal, causing a braking force to be applied to the motor until it comes to rest at the middle of the desired step. If the motor proceeds past the precise middle location, the drive voltage is reversed and the motor is returned quickly to the programmed location position. The output of operational amplifier 158 is passed through inverter 160 and motor drive circuit 162, and connected from there to the motor. As seen from the foregoing description, the motor control of this invention provides several distinct advantages. First, due to the unique converter design, means is provided for accurately determining without ambiguity the direction of rotation of the motor (this enables accurate and continuous tracking of the motor location, and thus of the carriage or other instrument which is being driven by the motor). Also, the digital circuitry provides a unique and highly efficient control for moving the motor from one position to a designated position with a maximum speed and efficiency. By defining a control range which is established, in the example of this embodiment, to be only one step (or any other short distance) from the designated location, the motor is moved as quickly as possible until the optimum time for deceleration. Once the motor is in the control range, the count of the increment counter corresponds to the position error, so this count movement is utilized to generate the control signal for braking the motor so that it stops at precisely the target location.

The invention has been illustrated with a system wherein the motor can be driven through 128 steps, which corresponds to a convenient binary number. However, with digital technique of this control the number of increments through which the motor can be driven can be made a design parameter and varied for the application. Likewise, the control range, or number of motor increments during which the speed of the motor is varied, can be made a design parameter within the scope of this invention.

We claim:

1. A motor control system for controlling movement of a motor which drives an element toward a destination position, comprising:
   a periodic means for generating a first periodic plural bit signal, each cycle of said plural bit signal corresponding to movement by said element of a first increment of distance, and for generating an increment signal each said cycle;
   counting means connected to receive said increment signal, for generating a second periodic plural bit signal, each cycle of said second signal corresponding to movement by said element of a second increment of distance,
   means for generating a third plural bit drive signal, including combining means for combining said first and second plural bit signals,
   means for enabling said combining means only when said element is within a given range from said destination, said range being a predetermined function of said second increment of distance, and
   means for driving said motor with said third plural bit drive signal.

2. A motor control system for controlling movement of a motor which drives an element which is to be accurately positioned, the system being characterized by:
   signal means connected to said motor for developing two respective periodic motor movement signals which are spaced in phase;
   logic means for generating a periodic two bit signal from said movement signals and for generating a direction signal once each cycle of said two bit signal, which direction signal indicates the direction of movement of said motor;
   position means connected to said logic means, for developing a first signal representative of cycles of said two bit signal and a second signal representative of the actual position of said motor;
   programmed destination means for developing a signal representative of a programmed position destination for said motor;
   differential means connected to receive inputs from said actual position means and said programmed destination means, for determining the motor difference between the present actual position and the programmed position;
   control range means connected to receive the output from said differential means, for detecting when said motor difference is outside of and when it is within a predetermined motor control range;
   digital control signal means for developing a plural bit digital control signal having more than two bits, said control signal being of a constant value when said motor is outside of said control range, and being a variable value when said difference is within said motor control range, said digital control signal means being connected to combine said two bit signal from said logic means and said first signal from said position means;
   a digital to analog convertor for converting said plural bit digital signal to an analog signal; and
   drive means for producing a drive signal from said analog signal for driving said motor, said drive means comprising a drive circuit for generating a drive signal component and a brake circuit for generating a brake signal component which is a function of the differential of said analog signal.

3. The motor control as described in claim 2, wherein said plural bit signal comprises a direction bit, and means connected to said differential means for generating said direction bit.

4. The motor control as described in claim 2, wherein said digital control signal means comprises first and second logic arrays which are connected to receive inputs from said differential means, which inputs enable operation of said arrays only when said motor difference is within said predetermined motor control range.

* * * * *